| (12) | United States Patent | (10) Patent No.: | US 8,891,730 B2 |
|---|---|---|---|
| | Kuesel | (45) Date of Patent: | Nov. 18, 2014 |

(54) APPARATUS FOR MONITORING THE CONNECTION OF A CONVEYOR BELT BY MEANS OF HIGH-ENERGY RAYS

(71) Applicant: Phoenix Conveyor Belt Systems GmbH, Bad Blankenburg (DE)

(72) Inventor: Bernd Kuesel, Hamburg (DE)

(73) Assignee: Phoenix Conveyor Belt Systems GmbH, Bad Blankenburg (DE)

( * ) Notice: Subject to any disclaimer, the term of this patent is extended or adjusted under 35 U.S.C. 154(b) by 158 days.

(21) Appl. No.: 13/738,680

(22) Filed: Jan. 10, 2013

(65) Prior Publication Data

US 2013/0129042 A1    May 23, 2013

Related U.S. Application Data

(63) Continuation of application No. PCT/EP2011/056533, filed on Apr. 26, 2011.

(30) Foreign Application Priority Data

Jul. 12, 2010 (DE) .......................... 10 2010 036 331

(51) Int. Cl.
*G01N 23/02* (2006.01)
*B65G 43/02* (2006.01)
*G01N 23/06* (2006.01)
*B65G 15/36* (2006.01)
*G01N 23/16* (2006.01)

(52) U.S. Cl.
CPC .............. *G01N 23/063* (2013.01); *B65G 43/02* (2013.01); *B65G 15/36* (2013.01); *G01N 23/16* (2013.01)
USPC ............................................ 378/58; 378/57

(58) Field of Classification Search
USPC ....................................................... 378/57, 58
See application file for complete search history.

(56) References Cited

U.S. PATENT DOCUMENTS

| 4,020,945 | A | 5/1977 | Takeno et al. |
|---|---|---|---|
| 5,291,131 | A | 3/1994 | Suzuki et al. |
| 6,291,991 | B1 * | 9/2001 | Schnell .......................... 324/235 |
| 7,427,767 | B2 | 9/2008 | Kemp |
| 8,149,989 | B2 | 4/2012 | Schnell |
| 2007/0058777 | A1 * | 3/2007 | Kondo ............................ 378/57 |

FOREIGN PATENT DOCUMENTS

| CN | 1936555 A | 3/2007 |
|---|---|---|
| DE | 35 17 314 A1 | 1/1986 |
| DE | 195 25 326 C1 | 10/1996 |
| DE | 10 2007 043 686 A1 | 3/2009 |
| JP | 4-158208 A | 6/1992 |
| JP | 2000-292371 A | 10/2000 |
| WO | WO 2008/034483 A1 | 3/2008 |

* cited by examiner

*Primary Examiner* — Hoon Song
(74) *Attorney, Agent, or Firm* — Walter Ottesen P.A.

(57) ABSTRACT

The invention is directed to an apparatus for continuous and non-destructive monitoring of the connection of a conveyor belt. During movement of the conveyor belt, a radiation source emits rays in the direction of the belt surface. The rays are of such high energy that they penetrate the conveyor belt and the connection thereof within a material-free region. A sensor detects the rays which have passed through. A process computer evaluates the result of the radiographic examination by comparing the actual connection values to set connection values and connection limit values. The radiation source and the sensor are accommodated in a housing. The housing has two openings between the radiation source and the sensor through which the moving conveyor belt passes without contact. The housing is integrated into the lower run of a conveyor system.

15 Claims, 5 Drawing Sheets

APPARATUS FOR MONITORING THE CONNECTION OF A CONVEYOR BELT BY MEANS OF HIGH-ENERGY RAYS

CROSS REFERENCE TO RELATED APPLICATIONS

This application is a continuation application, of international patent application PCT/EP2011/056533, filed Apr. 26, 2011, designating the United States and claiming priority from German application 10 2010 036 331.6, filed Jul. 12, 2010, and the entire content of both applications is incorporated herein by reference.

FIELD OF THE INVENTION

The invention relates to an apparatus for the continuous and nondestructive monitoring of the connection of a conveyor belt having a carrying-side cover plate and a running-side cover plate each made of an elastomer material and having an embedded tension member, wherein, during movement of the conveyor belt, a radiation source emits rays in the direction of the belt surface, which rays are of such high energy that they penetrate the conveyor belt and hence also its connection within a material-free region, wherein a sensor detects without contact the rays which have passed through. A process computer evaluates the result of the radiographic check, to be precise with detection of the actual connection values and comparison with the intended connection values and the connection limit values.

BACKGROUND OF THE INVENTION

The connections of conveyor belts are generally viewed as areas of a conveyor system which deserve particular attention with regard to their serviceability and durability. This resides in the fact that, in this area, the tensile forces of the tension member in the form of cords made of steel or aramid or in the form of a single-layer or multilayer fabric cross over into the elastomer material in the connection and in turn into the tension member of the following belt length. Here, the belt tensile force will load both the elastomer material with shear stresses and also the adhesion between the elastomer material and the tension member. It is additionally necessary to assume that the stress distribution within the connection and in the transition regions will not be homogeneous, so that there will always be areas from which failure of the connection can originate after a correspondingly long period of use.

Since the failure of a conveyor belt connection represents a very large potential hazard and a considerable economic risk, such events must be avoided. The operators of the conveyor belt systems therefore demand monitoring devices fox conveyor belt connections which give notice of a starting failure in good time and permit maintenance measures to be introduced before breakage of the connection occurs.

Apart from regular inspections, in which external damage is detected visually, continuous, automatic monitoring of the entire connection length or individual discrete zones of the connection is recommended, which, for example in the case of multi-stage steel cord belt connections, can be the deflection zones and what are known as repeats. Here, the starting point will be the supposition that, in normal operation (not under extreme overload!), a connection will not fail abruptly as a whole, rather that failure of individual areas in a connection will be assumed. In this case, the remaining intact, areas will experience a higher loading, which leads to higher stretch and therefore to an increase in the length of the loaded connection.

The lengths of the connection or reference section, measured at defined points in the conveyor belt system, must be compared with intended values and limiting values at which, if exceeded, a warning message is given or even a stoppage of the conveyor system is carried out.

Therefore, numerous developments are associated with the conveyor belt connection monitoring, reference being made in particular below to the following patent literature: DE 195 25 326 C1; U.S. Pat. No. 5,291,991; U.S. Pat. No. 4,020,945; and, U.S. Pat. No. 5,291,131.

The previously most important conveyor belt connection monitoring for use in large-scale conveyor systems is described by the document U.S. Pat. No. 6,291,991, wherein the monitoring system in this regard comprises the following components, specifically measuring marks, a measuring mark detection system, signal conditioning for the measuring mark detection system based on time measurement, an identification system with address, address detector and reader, a time measuring element, various measuring systems for determining the belt and ambient temperature and the belt tensile force and, finally, a process computer for the purpose of evaluating all the data.

The disadvantage in this case is the large number of monitoring components, individual components being susceptible to faults and, to some extent, also being difficult and costly to procure, which demonstrates the limits of the economic viability.

In the recent past, a monitoring device for conveyor belts by means of high-energy rays has therefore been advanced, which is described in particular in the following patent literature: DE 35 17 314 A1; U.S. Pat. No. 8,149,989; JP 04158208 A (Patent Abstracts of Japan); and, JP 2000292371 A (Patent Abstracts of Japan).

However, this development is still in its early stages, in particular with regard to conveyor belt connection monitoring.

SUMMARY OF THE INVENTION

The object of the invention is, then, to develop the apparatus according to U.S. Pat. No. 8,149,989 further in such a way that detection of both internal and external problems in the connection of a conveyor belt is possible. In addition, the intention hereby is for the position and geometry of the tension members vulcanized into the conveyor belt, in particular in the form of tension member cords, to be detected in the connection area.

Furthermore, the monitoring of the conveyor belt connection is to be capable of being carried out continuously and without interference from external influences and in an environmentally friendly manner.

The object, is achieved in that the radiation source and the sensor are accommodated in a housing, there being between the radiation source and the sensor two housing openings, through which the moving conveyor belt and its connection runs without contact.

The radiation source emits especially x-rays and is especially in the form of an x-ray tube. Within the housing, the radiation source is arranged in such a way that the belt surface can be covered by the rays in accordance with the three variants I, II and III described below.

Variant I

The radiation source covers the entire width of the conveyor belt and its connection. This is preferably the case when the conveyor belt is not excessively wide, for example up to 1000 mm.

Variant II

The radiation source covers only the two edge regions of the conveyor belt and its connection. If the conveyor belt is 2000 mm wide, for example, then the two edge regions having a dimension of 200 to 300 mm each are detected. In the case of steel cord conveyor belts, each edge region includes at least one cord repeat. In the case of textile conveyor belts, for example with a finger connection, the monitoring in each case reaches one finger end on each side.

In this variant, two separate radiation sources are used, in particular in the form of two separate x-ray tubes, each edge region being provided with one radiation source.

In particular during the exclusive measurement of the edge regions of a conveyor belt in accordance with Variant II, a high-resolution system comprising radiation source and sensor is used, since the distances between the cord ends that are to be detected at high speed are only a few centimeters.

Variant III

Large overland conveyor belts, for which the monitoring is of particular importance, are generally up to 2800 mm wide. Since, in particular, the x-ray tubes are relatively expensive, the conveyor belt is divided up into longitudinal strips (segments) when a single x-ray tube is used. If, for example, the conveyor belt has a width of 2000 mm, then this is divided up into four longitudinal strips each having a width of 500 mm. After each revolution, the x-ray tube is displaced by 500 mm. A 2000 mm wide conveyor belt and its connection would then be recorded completely in four revolutions.

Opposite the radiation source, that is to say on the other side of the moving conveyor belt, the rays are detected by sensors, also comprising light-sensitive chips. In order to obtain a good resolution, for example of 3 mm, even with a high speed of a conveyor belt, which is usually around 6 m/s, line sensors are preferably used. The sensor can also act as an individual sensor or as a sensor chain. The dimension of a sensor depends in particular on according to which of the three aforementioned Variants I, II or III the radiation source covers the extent of the conveyor belt width. In the case of Variant III, a displaceable sensor can be used.

The intensity of the received rays in conjunction with the subsequent evaluation of the gray values by specific image processing software permits conclusions to be drawn about the condition of the conveyor belt connection.

The data from the locations deviating from the satisfactory condition of the connection is finally evaluated in real time and automatically leads to fault messages, for example via individual threshold value data filters. In addition, the data is evaluated graphically.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
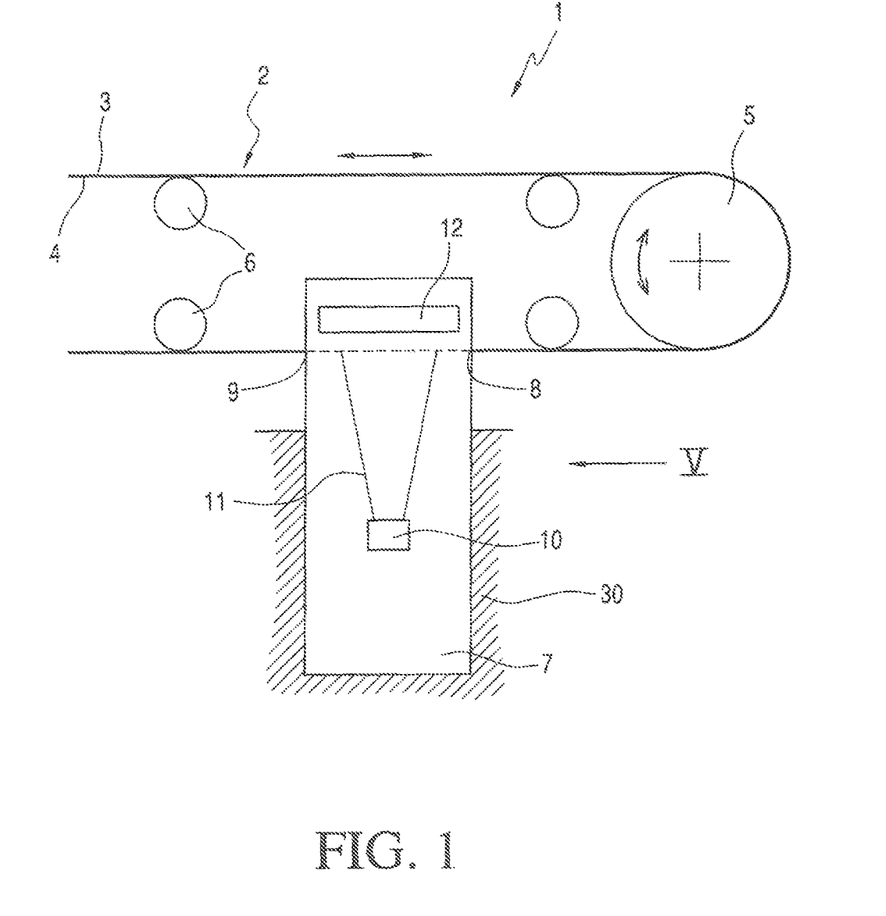
FIG. 1 shows the arrangement of a housing with integrated radiation source and sensor within a running conveyor system.

FIG. 1 shows a conveyor system 1 having a conveyor belt 2, which comprises a carrying-side cover plate 3 and a running-side cover plate 4 each made of an elastomer material, for example, a vulcanized rubber mixture based on CR, and an embedded tension member. The tension members used are cords made of steel or aramid extending in the longitudinal direction of the conveyor belt, cords made of steel being of particular significance. The tension member can also be a textile fabric, in particular a single-layer or multilayer fabric, for example a polyester-polyamide fabric. The tension member of a steel cord conveyor belt will be discussed in more detail in conjunction with FIG. 2.

In the running direction (arrow direction), the conveyor belt 2 is led around a drum 5 (drive drum, reversal drum). The running-side cover plate 4 is supported on support, rollers 6.

Incorporated in the conveyor system 1, within the lower run, is a housing 7 which has two housing openings 8 and 9, through which the moving conveyor belt 2 is guided in the running direction at normal operating speed. The two housing openings are normally formed as appropriately large wide slots, through which the conveyor belt free of goods conveyed thereon can be led without contact.

Figure 4:
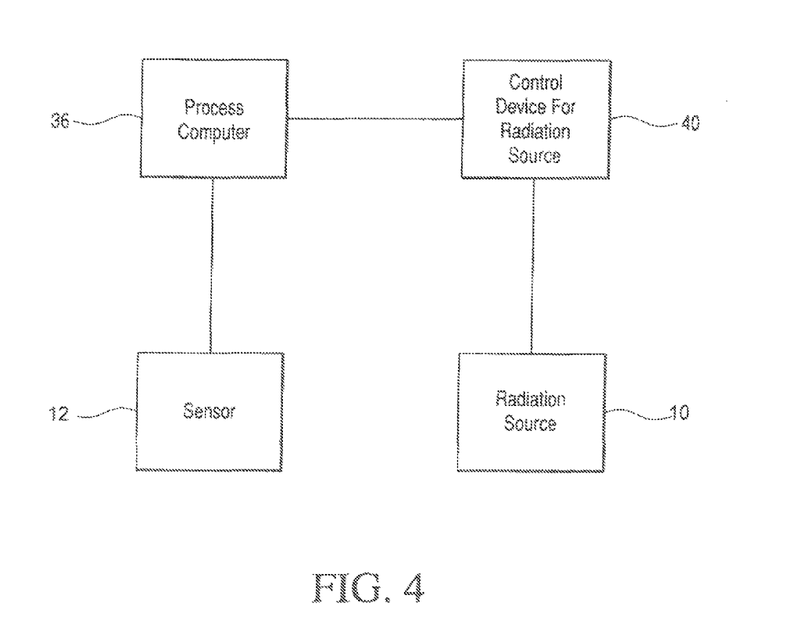
FIG. 4 is a schematic showing the process computer connected to the sensor and radiation source including the control device.

A radiation source 10, in particular in the form of an x-ray tube, is accommodated within the housing 7. The radiation source 10 with its high-energy rays 11, especially rays in the form of x-rays, detects and covers the carrying-side cover plate 3. With regard to the covering or detecting, reference is made to the three variants I, II or III described previously herein. A sensor 12, which is arranged in the immediate vicinity of the running-side cover plate 4, detects without contact (that is, without any wear) the rays 11 that have passed through. The sensor 12 is configured, in particular, as a line sensor. As FIG. 4 shows, a process computer 36 is connected to the sensor 12. The computer 36 is coupled with the radiation source 10 including its control device 40. The process computer 36 finally evaluates the result of the radiographic check.

The installation of the housing 7 for permanent use, in particular as a commercial x-ray device, is preferably carried out underneath the conveyor system 1, specifically sunk into the ground 30 as shown in FIG. 1. This is advantageous for the following reasons:

(a) the rays 11 possibly passing through the housing 7 are attenuated by the surrounding earth;
(b) the conveyor belt 2 is free of contamination there; and,
(c) the conveyor belt 2 can be led horizontally through the housing 7, which is practical for satisfactory radiography.

Figure 5:
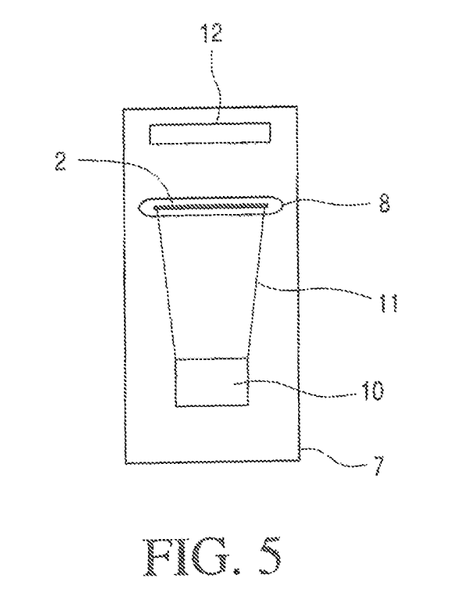
FIG. 5 is a side elevation view of the housing 7 viewed in the direction of arrow V in FIG. 1.

FIG. 5 is an elevation view of the housing 7 in the direction of arrow V of FIG. 1 and shows the conveyor belt 2 entering the housing 7 through opening 8.

The x-ray device that is preferably used can be linked online without difficulty, so that additional evaluations of the data found are possible from any desired locations in the world.

In the exemplary embodiment according to FIG. 1, a single housing with integrated radiation source and integrated sensor carries out the radiographic check, which is normally also sufficient. In the case of conveyor systems of large dimensions according to FIG. 1, it may be practical to use at least two housings, which are arranged at a relatively great distance from each other. In addition, a monitoring check is associated therewith.

Figure 2:
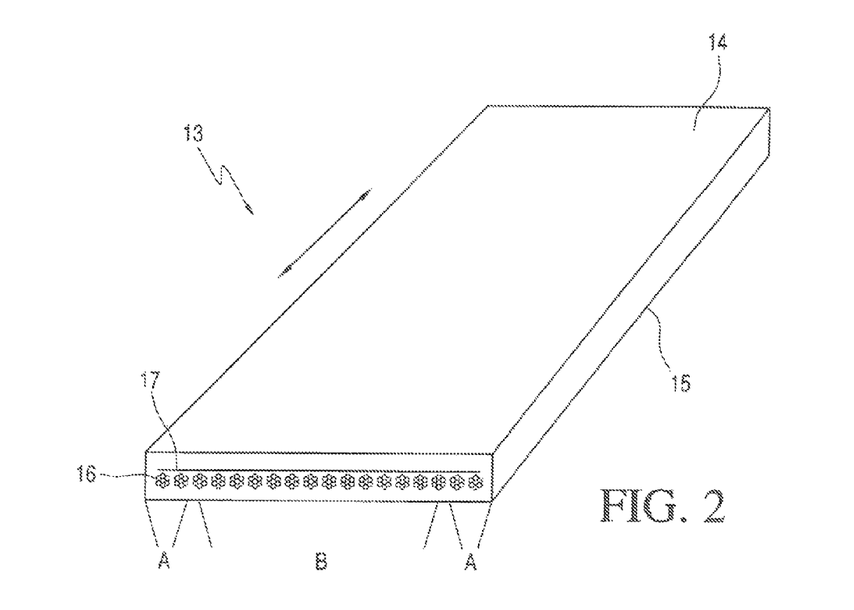
FIG. 2 shows the structure of a steel cord conveyor belt.

FIG. 2 now shows details of a conveyor belt 13 extending in the running direction narrow direction) and having a carrying-side cover plate 14, a running-side cover plate 15, an embedded reinforcement 16 in the form of steel cords extending in parallel and having transverse reinforcement 17 embedded within the carrying-side cover plate for the purpose of slit prevention. The transverse reinforcement is composed in particular of synthetic cords, for example made of polyamide, and extends substantially over the entire conveyor belt width (WO 2008/034483 A1).

Figure 6:
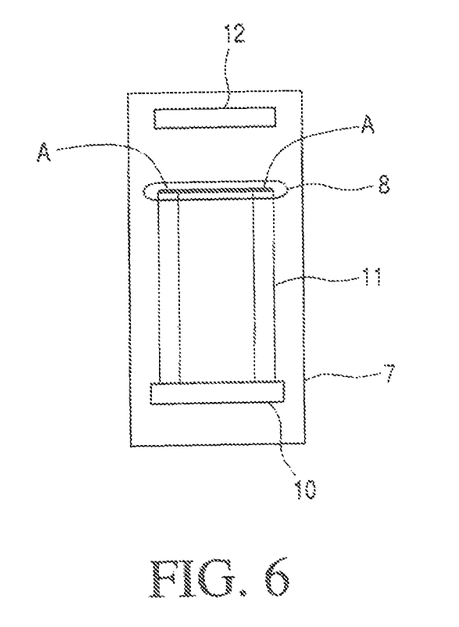
FIG. 6 is a side elevation view showing the radiation device arranged for covering the two side regions of the conveyor belt.

As a rule, the steel, cords within, the two edge regions A are subjected to higher loading by high belt tensile forces than the steel cords within the central region B. It is therefore normally sufficient to implement Variant II within the context of the radiographic check. In FIG. 6, a schematic shows how the radiation source 10 is configured to detect two edge regions A of the conveyor belt passing into the housing 7 through elongated opening 8.

Figure 8:
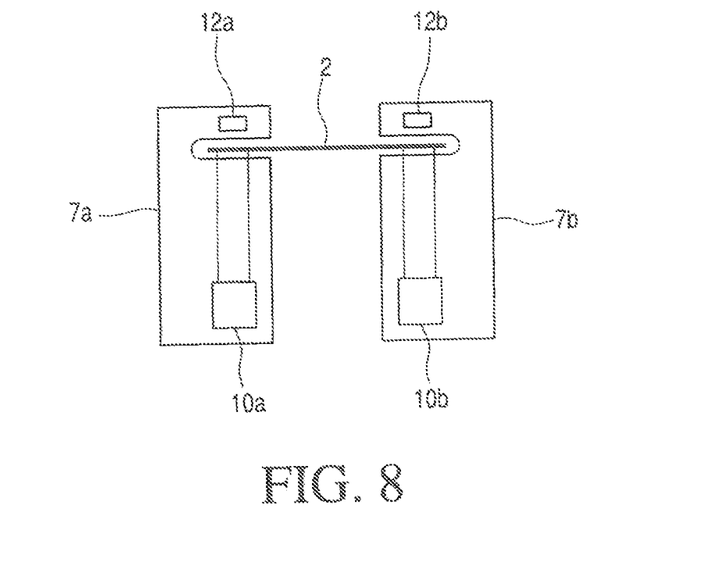

It is also possible to provide two housings (7a, 7b) as shown in FIG. 8. In this variant, two separate radiation sources (10a, 10b) can be used in the form of two separate x-ray tubes. Accordingly, two sensors (12a, 12b) are also provided for corresponding ones of the radiation sources (10a, 10b). In principle, however, Variants I and III can also be used with additional detection of the central region B.

Figure 7:
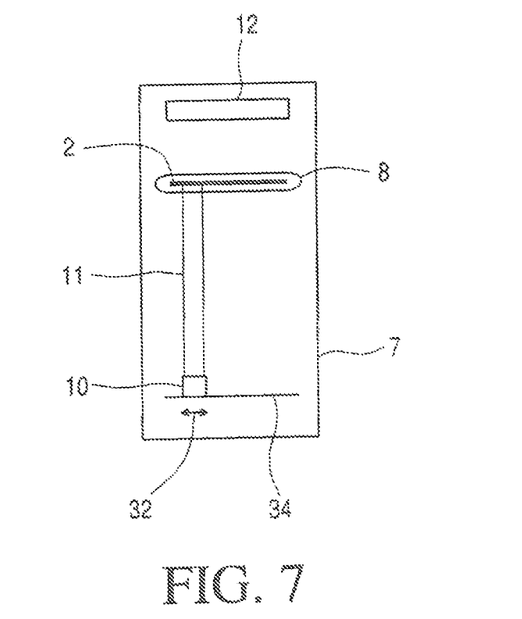
FIG. 7 shows a housing wherein the radiation source is movably mounted on a rail so as to be stepwise displaceable transversely to the direction of movement of the conveyor belt; and, FIG. 8 shows separate housings wherein radiographic checks are made on respective longitudinal edges of the conveyor belt.

For large overland conveyor belts, which are generally up to 2,800 mm wide, the conveyer belt can be thought of as being divided up into several longitudinal strips. After each revolution, the x-ray tube is displaced an incremental amount so that the longitudinal strips are covered sequentially. Thus, referring to FIG. 7, the radiation source 10 is movably mounted on a rail 34 so as to be stepwise displaceable in the directions of double arrow 32 transversely to the direction of movement of the conveyor belt 2. This configuration will permit the rays to foe directed sequentially toward corresponding ones of the longitudinal strips.

Figure 3:
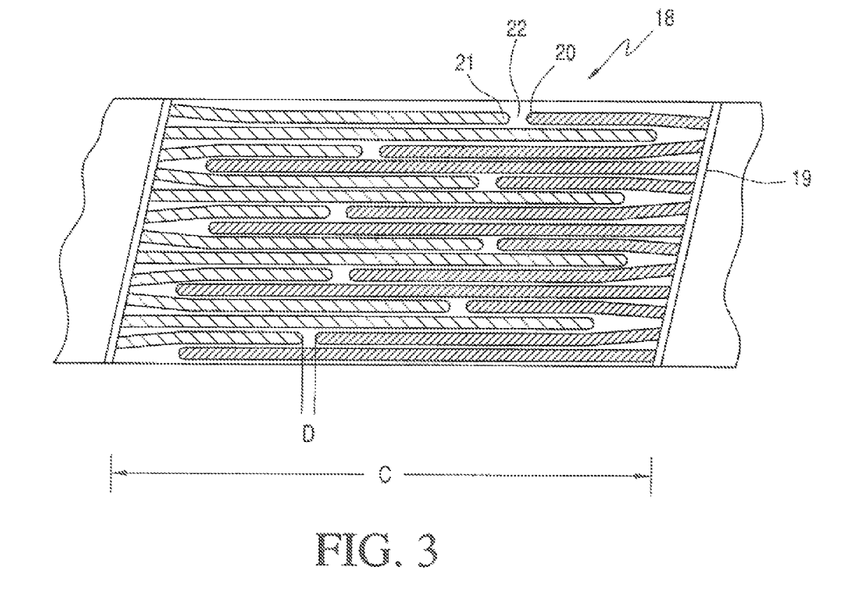
FIG. 3 shows the connection of a steel cord conveyor belt having cord repeats.

FIG. 3 shows the connection 18 of a steel cord conveyor belt. Within the connecting region C, the respective cord ends butt up against one another. In this embodiment, in each case three cord ends butting up against one another and having different cord end lengths form one cord repeat 19. This structural concept of the three cord ends butting up against one another then forms the basis for further cord repeats over the width of the steel cord conveyor belt. At the joint 22, the cord ends 20 and 21 conjointly define a spacing D.

During each revolution of the conveyor belt, the joints 22 of the steel cords of the connections are penetrated by radiation, in particular by x-rays, for example exclusively within the two edge regions A in accordance with Variant II (FIG. 2). The radiograph is stored in a computer and compared with the radiograph of the same connection from the previous revolution via a computing program. If the joints 22 of the steel cords differ beyond a predefined extent, an acoustic and/or visual signal or an automatic stoppage of the conveyor system is triggered by the software. Depending on the loaded state of the conveyer belt and the ambient temperature, the differences amount to some millimeters or centimeters. If a critical extent were reached, the connection would open, which ultimately can have catastrophic consequences.

The identification of the connections is carried out via embedded numbers or the like, which can be detected clearly in the radiograph, for example made of metal. The identification can also be carried out simply via the position, of the cord in the connection.

It is understood that the foregoing description is that of the preferred embodiments of the invention and that various changes and modifications may foe made thereto without departing from the spirit and scope of the invention as defined in the appended claims.

LIST OF DESIGNATIONS

Part of the Description

1 Conveyor system
2 Conveyor belt
3 Carrying-side cover plate
4 Running-side cover plate
5 Drum
6 Support rollers
7 Housing
7a, 7b Housings
8 Housing opening
9 Housing opening
10 Radiation source
10a, 10b Radiation sources
11 Rays
12 Sensor (detector)
12a, 12b Sensors
13 Conveyor belt
14 Carrying-side cover plate
15 Running-side cover plate
16 Tension member in the form of steel cords
17 Transverse reinforcement
18 Connection of the conveyor belt
19 Cord repeat
20 Cord end
21 Cord end
22 Joint of two cord ends
30 Earth
32 Double arrow
34 Rail
36 Process computer
40 Control device for radiation source
A Edge region of the conveyor belt
B Central region of the conveyor belt
C Connecting region of the conveyor belt
D Spacing of the cord ends

What is claimed is:

1. An apparatus for continuously and non-destructively monitoring a connection of a conveyor belt defining a belt surface and having a carrying side cover plate on which goods are carried and a running side cover plate with each of the cover plates being made of an elastomer material and having a reinforcement embedded therein, the apparatus comprising:

a radiation source for transmitting rays toward said belt surface during movement of the conveyor belt at a region of the conveyor belt free of the goods carried thereon;

said radiation source being configured to transmit said rays with sufficiently high energy so as to cause radiation to pass through said conveyor belt and the connection thereof within said region;

a sensor for detecting the radiation passed through said conveyor belt and said connection without contact therewith to carry out a radiographic check by providing actual values of said connection;

a processor for evaluating said radiographic check by comparing said actual values of said connection to set values and limit values of said connection;

a housing;

said radiation source and said sensor being disposed in said housing; and, first and second housing openings disposed between said radiation source and said sensor through which the moving conveyor belt and said connection thereof pass without contact.

2. The apparatus of claim 1, wherein said radiation source emits x-rays.

3. The apparatus of claim 2, wherein said radiation source is an x-ray tube.

4. The apparatus of claim 1, wherein said radiation source is arranged in said housing in such a way that said source covers the entire width of said conveyor belt and said connection thereof.

5. The apparatus of claim 1, wherein said radiation source comprises two radiation source units arranged in said housing in such a way that said radiation source covers the edge regions (A) of said conveyor belt and said connection thereof.

6. The apparatus of claim 1, wherein said conveyor belt and said connection thereof are subdivided into a plurality of imaginary longitudinal strips; and, said radiation source is step-wise displaceable transversely to the direction of movement of said conveyor belt and said connection thereof so as to permit said rays to foe directed sequentially toward corresponding ones of said longitudinal strips.

7. The apparatus of claim 1, wherein said radiation source covers said carrying-side cover plate and said sensor covers said running-side cover plate.

8. The apparatus of claim 1, wherein said sensor is a line sensor.

9. The apparatus of claim 1, wherein said sensor is an individual sensor.

10. The apparatus of claim 1, wherein said sensor comprises a sensor chain.

11. The apparatus of claim 1, wherein said housing openings for the moving conveyor belt are wide slots.

12. The apparatus of claim 1, wherein said housing is arranged at the lower run of the conveyor belt and said connection thereof.

13. The apparatus of claim 12, wherein said housing is sunk into the ground.

14. The apparatus of claim 1, wherein said housing is a single housing with said radiation source and said sensor being integrated therein to carry out said radiographic check.

15. An apparatus for continuously and non-destructively monitoring a connection of a conveyor belt defining a belt surface and having a carrying side cover plate on which goods are carried and a running side cover plate with each of the cover plates being made of an elastomer material and having a reinforcement embedded therein, the apparatus comprising:

two mutually separate housings;

a radiation source mounted in each one of said housings for transmitting rays toward said belt surface during movement of the conveyor belt at a region of the conveyor belt free of the goods carried thereon;

said radiation source being configured to transmit said rays with sufficiently high energy so as to cause radiation to pass through said conveyor belt and the connection thereof within said region;

a sensor mounted in each one of said housings for detecting the radiation passed through said conveyor belt and said connection without contact therewith to carry out a radiographic check by providing actual values of said connection;

an opening formed in each one of said housings disposed between the radiation source mounted therein and the sensor mounted therein, through which the moving conveyor belt and said connection thereof pass without contact; and, a processor for evaluating the radiographic check of each of said sensors by comparing the actual values of said connection to set values and limit values of said connection.

* * * * *

UNITED STATES PATENT AND TRADEMARK OFFICE
CERTIFICATE OF CORRECTION

PATENT NO. : 8,891,730 B2
APPLICATION NO. : 13/738680
DATED : November 18, 2014
INVENTOR(S) : Bernd Kuesel It is certified that error appears in the above-identified patent and that said Letters Patent is hereby corrected as shown below:

In the Specification,

In Column 1:
Line 54: delete "fox" and substitute -- for -- therefor.

In Column 5:
Line 14: delete "narrow" and substitute -- (arrow -- therefor.
Line 39: delete "conveyer" and substitute -- conveyor -- therefor.
Line 47: delete "foe" and substitute -- be -- therefor.

In Column 6:
Line 1: delete "conveyer" and substitute -- conveyor -- therefor.
Line 8: delete "position," and substitute -- position -- therefor.
Line 12: delete "foe" and substitute -- be -- therefor.

In the Claims,

In Column 7:
Line 32: delete "foe" and substitute -- be -- therefor.

Signed and Sealed this
Fourteenth Day of April, 2015

Michelle K. Lee
*Director of the United States Patent and Trademark Office*